(12) United States Patent
Hsu

(10) Patent No.: US 8,927,767 B2
(45) Date of Patent: Jan. 6, 2015

(54) CRYSTALLINE POLYMORPHS OF ACETYL-GLYCINE-BETA-ALANINE AND PROCESS OF MAKING THE SAME

(71) Applicant: Corum Inc., Taipei (TW)

(72) Inventor: Nai-Hsuan Hsu, Taipei (TW)

(73) Assignee: Corum Inc., Taipei (TW)

( * ) Notice: Subject to any disclaimer, the term of this patent is extended or adjusted under 35 U.S.C. 154(b) by 0 days.

(21) Appl. No.: 14/270,557

(22) Filed: May 6, 2014

(65) Prior Publication Data

US 2014/0336413 A1    Nov. 13, 2014

Related U.S. Application Data

(60) Provisional application No. 61/820,820, filed on May 8, 2013.

(51) Int. Cl.
*C07C 237/22*    (2006.01)

(52) U.S. Cl.
CPC .................................. *C07C 237/22* (2013.01)
USPC .......................................................... 562/564

(58) Field of Classification Search
USPC .......................................................... 562/564
See application file for complete search history.

(56) References Cited

U.S. PATENT DOCUMENTS

2013/0195782 A1*    8/2013    Hsu et al. ........................ 424/62

* cited by examiner

*Primary Examiner* — Shailendra Kumar
(74) *Attorney, Agent, or Firm* — WPAT, PC; Justin King

(57) ABSTRACT

This invention discloses novel crystalline polymorphs of acetyl-glycine-beta-alanine and process of making the same. The mentioned crystalline polymorphs can exhibit excellent purity and storage stability according to this invention. Therefore, the mentioned crystalline polymorphs can be applied in topical cosmetic compositions, pharmaceutical compositions as skin care preparations, or other functional preparations.

19 Claims, 4 Drawing Sheets

CRYSTALLINE POLYMORPHS OF ACETYL-GLYCINE-BETA-ALANINE AND PROCESS OF MAKING THE SAME

This application claims benefit of 61/820,820, filed on May 8, 2013.

BACKGROUND OF THE INVENTION

1. Field of the Invention

The present invention is generally related to a novel crystalline polymorph, and more particularly to crystalline polymorphs of acetyl-glycine-beta-alanine and process of making the same.

2. Description of the Prior Art

The application and synthesis of acetyl-glycine-beta-alanine as the following structure (1) was disclosed in WO 2012/051741A1 and U.S. patent application Ser. No. 13/128,446.

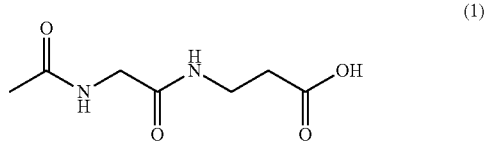

(1)

Acetyl-glycine-beta-alanine was taught to be capable of inhibiting melanin formation and exhibited good color stability in the cosmetic formulation in U.S. patent application Ser. No. 13/128,446.

Recently, more study about the mechanism of inhibiting melanin formation was completed and the results showed acetyl-glycine-beta-alanine down-regulated a key regulator of melanin synthesis (MITF) expression −37% and also reduced tyrosinase, TRP-1, and TRP-2 protein level at −41%, −41%, and −75% respectively. Ex vivo test in a tissue model of the human epidermis prepared from cultured human keratinocytes and melanocytes showed 2% of acetyl-glycine-beta-alanine exhibited excellent whitening efficacy (existing melanin level: −30%) in 9 day. In vivo human study also showed spot-brightening (51.67% age spot reduction) after 14 days. In another in vitro study for evaluating anti-inflammation effect, acetyl-glycine-beta-alanine also showed reduced IL-6 and IL8 level after exposure of human epidermal keratinocytes on UVB light.

A method of synthesis of acetyl-glycine-beta-alanine was described in U.S. patent application Ser. No. 13/128,446. The crude acetyl-glycine-beta-alanine which was obtained by concentration after hydrogenation was a mixed crystalline polymorph and its HPLC purity was only more than 95%. However, for active ingredients used in cosmetic and pharmaceutical industries, it is always required that higher HPLC purity more than 99%, stable crystalline polymorph and excellent storage stability. As a result, there is a need for developing a stable crystalline polymorph of acetyl-glycine-beta-alanine, which is more suitable for its application.

SUMMARY OF THE INVENTION

In light of the above background, in order to fulfill the requirements of the industry, the present invention provides novel crystalline polymorphs of acetyl-glycine-beta-alanine and process of making the same having the adventures of exhibiting excellent purity and storage stability, so that the acetyl-glycine-beta-alanine can be applied in various compositions.

We have discovered novel crystalline polymorphs of acetyl-glycine-beta-alanine and process of making the same.

In accordance with one embodiment of the present invention, the crystalline polymorph A of acetyl-glycine-beta-alanine exhibits a powder X-ray diffraction pattern having peaks at 10.4±0.2, 11.0±0.2, 12.9±0.2, 16.0±0.2, 16.4±0.2, 17.6±0.2, 19.1±0.2, 19.5±0.2, 20.0±0.2, 21.2±0.2, 23.2±0.2, 23.5±0.2, 24.1±0.2, 24.9±0.2, 25.3±0.2, 26.2±0.2, 27.9±0.2, 30.2±0.2, 39.5±0.2 and 40.1±0.2 2-theta degree.

In accordance with yet another embodiment of the present invention, Fourier transform infrared spectrum of the crystalline polymorph A of acetyl-glycine-beta-alanine having bands at 3315±2 $cm^{-1}$, 1697±2 $cm^{-1}$, 1670±2 $cm^{-1}$, 1543±2 $cm^{-1}$, 1441±2 $cm^{-1}$, 1376±2 $cm^{-1}$, 1277±2 $cm^{-1}$, 1248±2 $cm^{-1}$, 1144±2 $cm^{-1}$, 1089±2 $cm^{-1}$, 1071±2 $cm^{-1}$, 1044±2 $cm^{-1}$, 998±2 $cm^{-1}$, 983±2 $cm^{-1}$, 949±2 $cm^{-1}$, 888±2 $cm^{-1}$, 796±2 $cm^{-1}$, 712±2 $cm^{-1}$, 666±2 $cm^{-1}$.

In accordance with yet another embodiment of the present invention, differential scanning calorimetry (DSC) thermogram of the crystalline polymorph A of acetyl-glycine-beta-alanine indicated two endotherm peaks at 168±2° C. and 177±2° C.

In accordance with yet another embodiment of the present invention, we developed a process of making crystalline polymorph A of acetyl-glycine-beta-alanine, which comprises:

(1) Dissolving a crude of acetyl-glycine-beta-alanine in water and filtering the insoluble particles to obtain a acetyl-glycine-beta-alanine aqueous solution.

(2) Concentrating the acetyl-glycine-beta-alanine aqueous solution of (1) to a residue and adding a solvent and water to form a mixture. Heating the mixture from 40 to 100° C. The weight ratio of the solvent and water was from 10:0.01 to 4:1. The preferred weight ratio of the solvent and water was from 10:0.1 to 10:1.

(3) The solvent applied in (2) was selected from the group consisting of methanol, ethanol, isopropanol, and propanol. The most preferred solvent of the above was isopropanol.

(4) Forming the crystalline by cooling down the mixture of (2) to about −10 to 20° C., filtering the crystalline and drying the crystalline under vacuum. The crystalline was crystalline polymorph A of acetyl-glycine-beta-alanine.

In accordance with one embodiment of the present invention, the crystalline polymorph B of acetyl-glycine-beta-alanine exhibit a powder X-ray diffraction pattern having peaks at 9.3±0.2, 15.1±0.2, 16.5±0.2, 21.3±0.2, 22.4±0.2, 23.2±0.2, 24.6±0.2, 25.2±0.2, 26.1±0.2, 28.6±0.2, 30.4±0.2, 31.0±0.2, 32.1±0.2, 38.4±0.2, 40.0±0.2 and 41.6±0.2 2-theta degree.

In accordance with yet another embodiment of the present invention, Fourier transform infrared spectrum of the crystalline polymorph B of acetyl-glycine-beta-alanine having bands at 3309±2 $cm^{-1}$, 1699±2 $cm^{-1}$, 1662±2 $cm^{-1}$, 1601±2 $cm^{-1}$, 1548±2 $cm^{-1}$, 1436±2 $cm^{-1}$, 1375±2 $cm^{-1}$, 1313±2 $cm^{-1}$, 1265±2 $cm^{-1}$, 1206±2 $cm^{-1}$, 1132±2 $cm^{-1}$, 1080±2 $cm^{-1}$, 1046±2 $cm^{-1}$, 1014±2 $cm^{-1}$, 912±2 $cm^{-1}$, 786±2 $cm^{-1}$, 736±2 $cm^{-1}$, 688±2 $cm^{-1}$.

In accordance with yet another embodiment of the present invention, differential scanning calorimetry (DSC) thermogram of the crystalline polymorph B of acetyl-glycine-beta-alanine indicated one endotherm peak at 176±2° C.

In accordance with yet another embodiment of the present invention, we developed a process of making crystalline polymorph B of acetyl-glycine-beta-alanine, which comprises:

(1) To form a mixture by mixing a crude of acetyl-glycine-beta-alanine obtained from concentrating a crystallization mother liquid with isopropanol and water at room temperature. The ratio of the isopropanol and water is from 10:1 to 20:1.

(2) Dissolving the mixture of (1) at 65 to 80° C. to form a solution.

(3) Cooling the solution of (2) to form a crystalline at 10 to 30° C.

(4) Filtering the crystalline of (3) and drying the crystalline under vacuum to obtain the crystalline polymorph B of acetyl-glycine-beta-alanine.

Both the crystalline polymorph A and polymorph B of acetyl-glycine-beta-alanine discussed above in an effective amount can be formulated in cosmetics composition and other topical composition.

Accordingly, the present invention discloses novel crystalline polymorphs of acetyl-glycine-beta-alanine and process of making the same. The crystalline polymorphs of acetyl-glycine-beta-alanine can exhibit different character on the detected spectrum. Furthermore, the process of forming the crystalline polymorphs of acetyl-glycine-beta-alanine can provide the crystalline polymorphs of acetyl-glycine-beta-alanine with excellent purity and stability, so that the crystalline polymorphs can be applied in topical cosmetic compositions, pharmaceutical compositions as skin care preparations, or other functional preparations.

BRIEF DESCRIPTION OF THE DRAWINGS

The present disclosure can be described by the embodiments given below. It is understood, however, that the embodiments below are not necessarily limitations to the present disclosure, but are used to a typical implementation of the invention.

DESCRIPTION OF THE PREFERRED EMBODIMENTS

Figure 1:
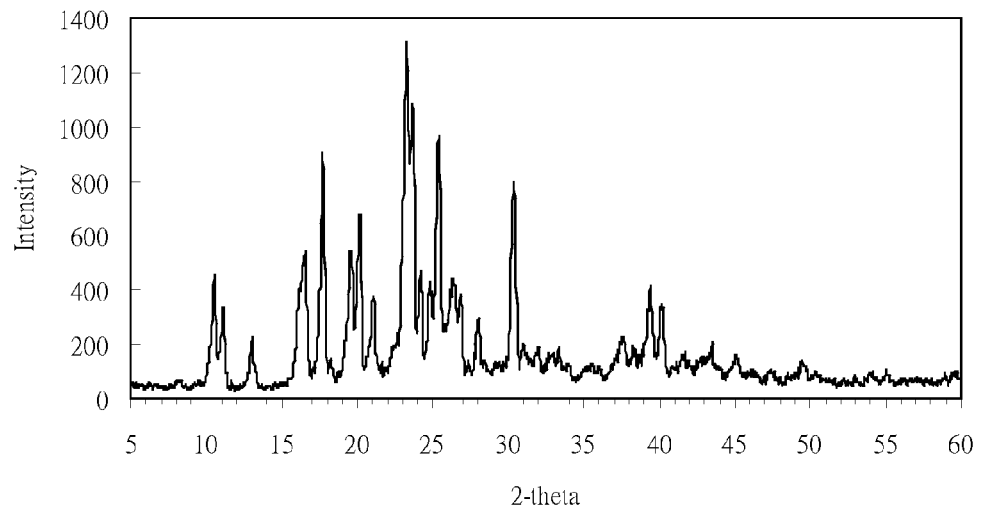
FIG. 1 is a characteristic powder X-ray diffraction pattern of crystalline polymorph A of acetyl-glycine-beta-alanine.

What probed into the invention is crystalline polymorphs of acetyl-glycine-beta-alanine and process of making the same. Detailed descriptions of the structure and elements will be provided in the following in order to make the invention thoroughly understood. Obviously, the application of the invention is not confined to specific details familiar to those who are skilled in the art. On the other hand, the common structures and elements that are known to everyone are not described in details to avoid unnecessary limits of the invention. Some preferred embodiments of the present invention will now be described in greater details in the following. However, it should be recognized that the present invention can be practiced in a wide range of other embodiments besides those explicitly described, that is, this invention can also be applied extensively to other embodiments, and the scope of the present invention is expressly not limited except as specified in the accompanying claims.

One preferred embodiment according to this specification discloses novel crystalline polymorphs of acetyl-glycine-beta-alanine. And, the crystalline polymorphs of acetyl-glycine-beta-alanine can be identified with powder X-ray diffraction, Fourier transform infrared spectroscopy (FTIR), and differential scanning calorimetry (DSC).

Another preferred embodiment according to this specification discloses a process for forming novel crystalline polymorphs of acetyl-glycine-beta-alanine. And, the crystalline polymorphs of acetyl-glycine-beta-alanine can be identified with powder X-ray diffraction, Fourier transform infrared spectroscopy (FTIR), and differential scanning calorimetry (DSC).

In accordance with one embodiment of the present invention, a crystalline polymorph A of acetyl-glycine-beta-alanine is disclosed. The crystalline polymorph A of acetyl-glycine-beta-alanine is characterized with powder X-ray diffraction pattern comprising peaks at 10.4±0.2, 11.0±0.2, 12.9±0.2, 16.0±0.2, 16.4±0.2, 17.6±0.2, 19.1±0.2, 19.5±0.2, 20.0±0.2, 21.2±0.2, 23.2±0.2, 23.5±0.2, 24.1±0.2, 24.9±0.2, 25.3±0.2, 26.2±0.2, 27.9±0.2, 30.2±0.2, 39.5±0.2, and 40.1±0.2 2-theta degree.

In accordance with yet another embodiment of the present invention, Fourier transform infrared spectrum of the crystalline polymorph A of acetyl-glycine-beta-alanine having bands at 3315±2 $cm^{-1}$, 1697±2 $cm^{-1}$, 1670±2 $cm^{-1}$, 1543±2 $cm^{-1}$, 1441±2 $cm^{-1}$, 1376±2 $cm^{-1}$, 1277±2 $cm^{-1}$, 1248±2 $cm^{-1}$, 1144±2 $cm^{-1}$, 1089±2 $cm^{-1}$, 1071±2 $cm^{-1}$, 1044±2 $cm^{-1}$, 998±2 $cm^{-1}$, 983±2 $cm^{-1}$, 949±2 $cm^{-1}$, 888±2 $cm^{-1}$, 796±2 $cm^{-1}$, 712±2 $cm^{-1}$, 666±2 $cm^{-1}$.

In accordance with yet another embodiment of the present invention, differential scanning calorimetry (DSC) thermogram of the crystalline polymorph A of acetyl-glycine-beta-alanine indicated two endotherm peaks at 168±2° C. and 177±2° C.

In accordance with yet another embodiment of the present invention, we developed a process of making crystalline polymorph A of acetyl-glycine-beta-alanine, which comprises:

(1) Dissolving a crude of acetyl-glycine-beta-alanine in water and filtering the insoluble particles to obtain a acetyl-glycine-beta-alanine aqueous solution.

(2) Concentrating the acetyl-glycine-beta-alanine aqueous solution of (1) to a residue and adding a solvent and water to form a mixture. Heating the mixture from 40 to 100° C. The weight ratio of the solvent and water was from 10:0.01 to 4:1. The preferred weight ratio of the solvent and water was from 10:0.1 to 10:1.

(3) The solvent applied in (2) was selected from the group consisting of methanol, ethanol, isopropanol, and propanol. The most preferred solvent of the above was isopropanol.

(4) Forming the crystalline by cooling down the mixture of (2) to about −10 to 20° C., filtering the crystalline and drying the crystalline under vacuum. The crystalline was crystalline polymorph A of acetyl-glycine-beta-alanine.

In accordance with yet another embodiment of the present invention, a crystalline polymorph B of acetyl-glycine-beta-alanine is disclosed. The Fourier transform infrared spectrum of the crystalline polymorph B of acetyl-glycine-beta-alanine having bands at about 3309±2 cm$^{-1}$, 1699±2 cm$^{-1}$, 1662±2 cm$^{-1}$, 1601±2 cm$^{-1}$, 1548±2 cm$^{-1}$, 1436±2 cm$^{-1}$, 1375±2 cm$^{-1}$, 1313±2 cm$^{-1}$, 1265±2 cm$^{-1}$, 1206±2 cm$^{-1}$, 1132±2 cm$^{-1}$, 1080±2 cm$^{-1}$, 1046±2 cm$^{-1}$, 1014±2 cm$^{-1}$, 912±2 cm$^{-1}$, 786±2 cm$^{-1}$, 736±2 cm$^{-1}$, 688±2 cm$^{-1}$.

In accordance with yet another embodiment of the present invention, differential scanning calorimetry (DSC) thermogram of the crystalline polymorph B of acetyl-glycine-beta-alanine indicated one endotherm peak at about 176±2° C.

In accordance with yet another embodiment of the present invention, we developed a process of making crystalline polymorph B of acetyl-glycine-beta-alanine, which comprises:

(1) To form a mixture by mixing a crude solid of acetyl-glycine-beta-alanine obtained from concentrating the crystallization mother liquid with isopropanol and water at room temperature. The weight ratio of isopropanol and water is from 10:1 to 20:1.

(2) Dissolving the mixture of (1) at 65 to 80° C. to form a solution.

(3) Cooling the solution of (2) to form a crystalline at 10 to 30° C.

(4) Filtering the crystalline of (3) and drying the crystalline under vacuum to obtain the crystalline polymorph B of acetyl-glycine-beta-alanine.

Both the crystalline polymorph A and polymorph B of acetyl-glycine-beta-alanine discussed above in an effective amount can be formulated in cosmetics composition and other topical composition.

In the following examples, all of the crystalline polymorphs of acetyl-glycine-beta-alanine were characterized by powder X-ray diffraction, Fourier transform infrared spectroscopy (FTIR), and differential scanning calorimetry (DSC).

The procedure of powder X-ray diffraction test used for obtaining FIG. 1, FIG. 2, FIG. 7 and FIG. 8 is described as follows:

The crystalline polymorphs of acetyl-glycine-beta-alanine was analyzed by an X-ray powder Diffractometer, Bruker D8 Advanced, equipped with a Cu anode (λ=1.540600 Angstrom). X-ray source operated at 40 kV, 40 mA. The measuring 2-theta range was from about 5 to 60 degree and step width was 0.05 degree.

Figure 3:
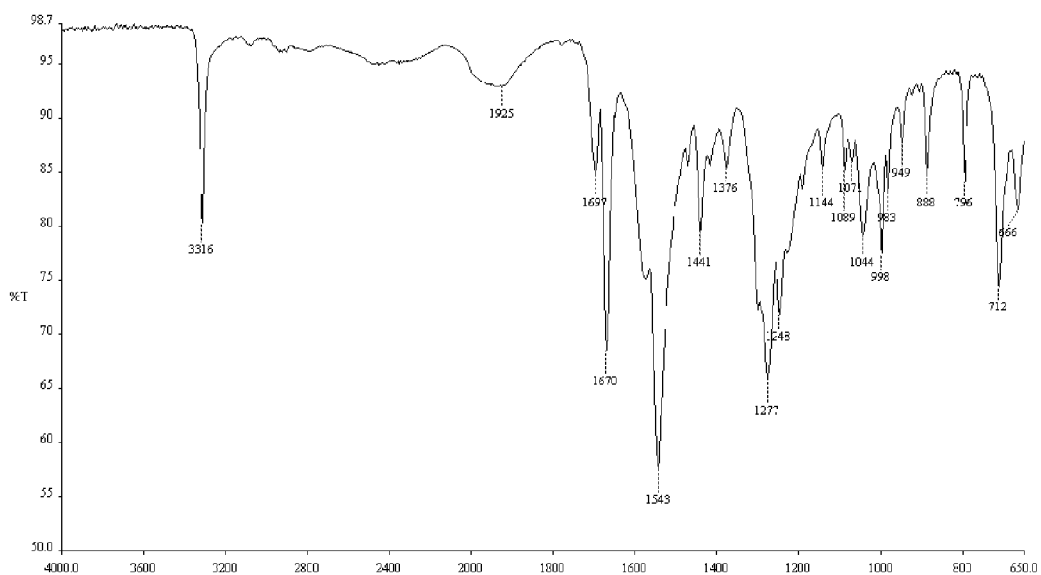
FIG. 3 is a characteristic Fourier transform infrared spectrum (FTIR) of crystalline polymorph A of acetyl-glycine-beta-alanine.
Figure 4:
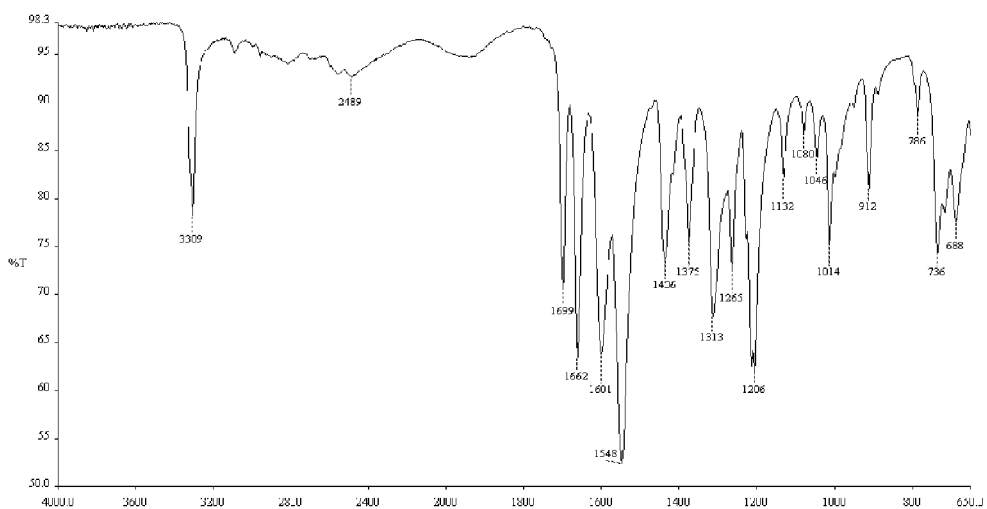
FIG. 4 is a characteristic Fourier transform infrared spectrum (FTIR) of crystalline polymorph B of acetyl-glycine-beta-alanine.

The general procedure for obtained Fourier transform infrared spectrum as shown as FIG. 3 and FIG. 4 is as follows:

A spectrometer, PerkinElmer Spectrum 100FT-IR, was used for obtaining the infrared spectrum of the crystalline polymorphs of acetyl-glycine-beta-alanine. The test sample was previously dried and ground into a fine powder. A small amount of the test sample was placed on the crystal of ATR directly. Set the micrometer screw to 2.0 to apply pressure to the sample. The infrared spectrum was obtained over the range of 4000 to 650 cm$^{-1}$.

Figure 5:
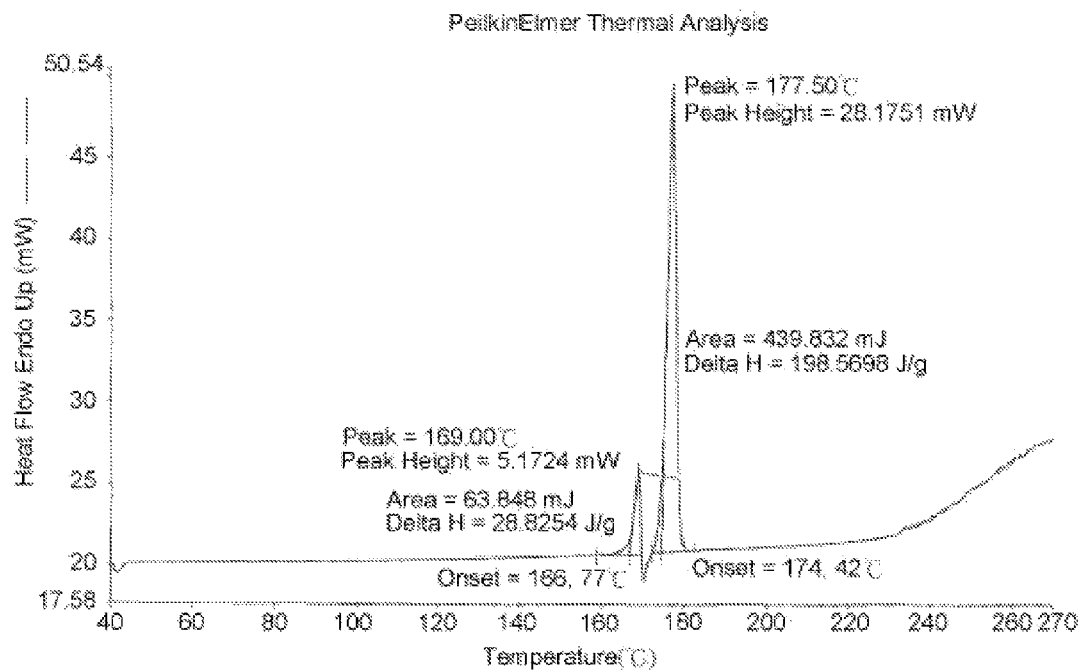
FIG. 5 is a characteristic differential scanning calorimetry (DSC) thermogram of crystalline polymorph A of acetyl-glycine-beta-alanine.
Figure 6:
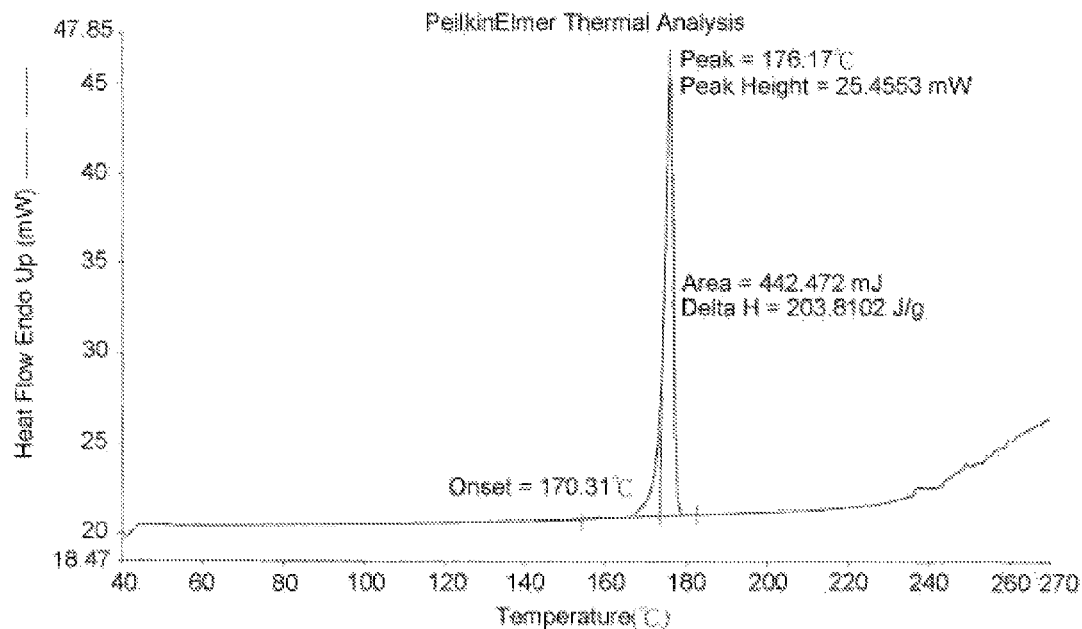
FIG. 6 is a characteristic differential scanning calorimetry (DSC) thermogram of crystalline polymorph B of acetyl-glycine-beta-alanine.
Figure 7:
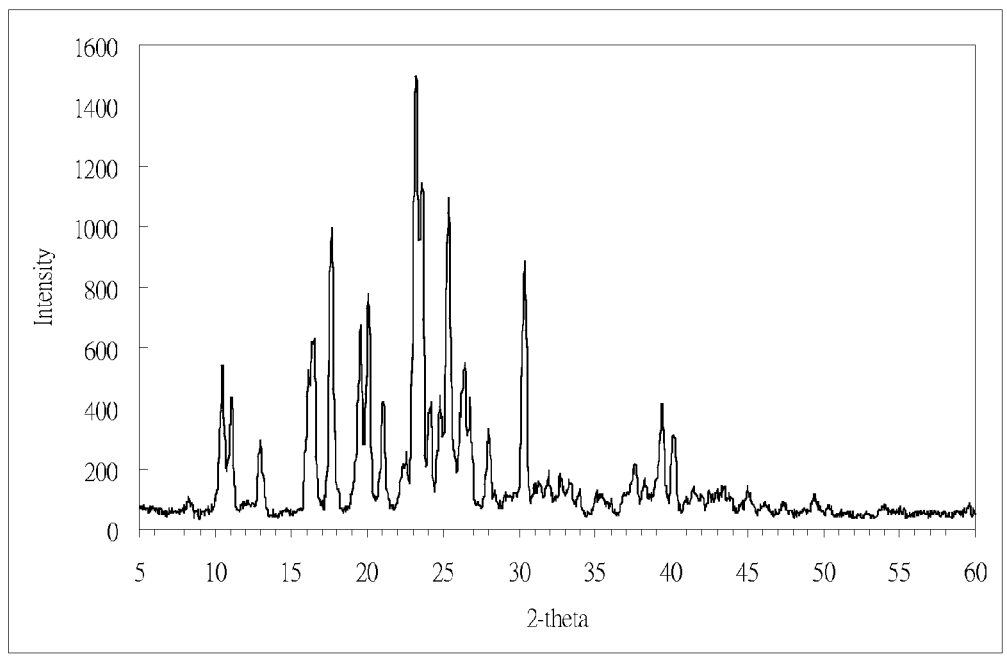
FIG. 7 is a characteristic powder X-ray diffraction pattern of crystalline polymorph A of acetyl-glycine-beta-alanine storage in an oven at 140° C. with air circulation for 4 hours.
Figure 8:
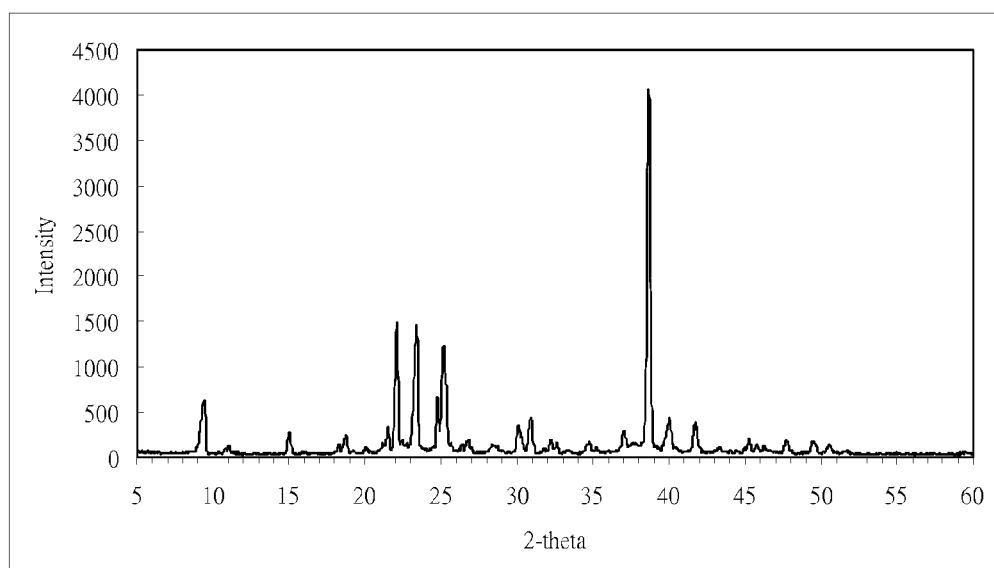
FIG. 8 is a characteristic powder X-ray diffraction pattern of crystalline polymorph B of acetyl-glycine-beta-alanine storage in an oven at 140° C. with air circulation for 4 hours.

The general procedure for obtained differential scanning calorimetry (DSC) thermogram as shown as FIG. 5 and FIG. 6 is as follows:

The test sample 2.000~3.000 mg was used to analyze its thermogram by the machine, Perkinelmer analyzer. In the test process, the test sample was heated from about 40 to 270° C. at heating rate as 10° C./min under nitrogen.

Preparation of Crude Acetyl-Glycine-Beta-Alanine

Acetyl-glycine-beta-alanine benzyl ester 50 grams was dissolved in isopropanol/H$_2$O (350/150 grams), and then 10% Pd/C (0.25 grams) was added. The mixture was stirred under hydrogen. After overnight, Pd/C was removed by filtration, and the resulting filtrate was concentrated to obtain a residue. Isopropanol (300 g) was added to the residue to from a mixture. The mixture was heated to 70-75° C. with stirring and then cooled to 15 to 20° C., the solid therein was isolated by filtration. The solid was dried under vacuum and white powder was obtained. The purity of the white powder is 98.5%, determined by HPLC.

A. Preparation of the Crystalline Polymorph A of Acetyl-Glycine-Beta-Alanine

Example 1

20 grams of crude acetyl-glycine-beta-alanine was dissolved in water (100 grams) and filtered to remove insoluble particles. The filtrate was concentrated to a residue and isopropanol/water (200 grams/20 grams) was added to the residue to form a mixture. The mixture was heated to about 70° C. and filtered to remove the insoluble particles in the mixture to obtain a solution. The solution was allowed to cool down for forming crystalline polymorph A of acetyl-glycine-beta-alanine, and those crystalline polymorph A of acetyl-glycine-beta-alanine are subsequently filtered at about 5° C. and dried under vacuum. 16.7 grams of the crystalline polymorph A of acetyl-glycine-beta-alanine was obtained. According to HPLC analysis, the purity of the obtained crystalline polymorph A was 99.9% (wavelength at 214 nm).

Example 2

20 grams of crude acetyl-glycine-beta-alanine obtained after hydrogenation was dissolved in water (100 grams), and filtered to remove insoluble particles. The filtrate was concentrated to obtain a residue, and 200 grams of isopropanol containing 0.23% moisture (measured by Karl-Fisher Titration) was added into the residue to form a mixture. The mixture was heated to reflux and then was allowed to cool down for forming crystalline polymorph A of acetyl-glycine-beta-alanine. The crystalline polymorph A of acetyl-glycine-beta-alanine was filtered at about 15° C. and was dried under vacuum. 17.5 grams of the crystalline polymorph A of acetyl-glycine-beta-alanine was obtained. According to HPLC analysis, the purity of the obtained crystalline polymorph A of acetyl-glycine-beta-alanine was 99.2% (wavelength at 214 nm).

Example 3

3 grams of crude acetyl-glycine-beta-alanine obtained after hydrogenation was dissolved in water (100 grams) and filtered to remove insoluble particles. The filtrate was concentrated to obtain a residue and ethanol/water (14.25 grams/0.75 grams) was added to the residue to form a mixture. The mixture was heated to about 75° C. and then was allowed to cool down for forming crystalline polymorph A of acetyl-glycine-beta-alanine. The crystalline polymorph A of acetyl-glycine-beta-alanine was filtered at about 10° C. and was subsequently dried under vacuum. 2.4 grams of the crystalline polymorph A of acetyl-glycine-beta-alanine was obtained. According to HPLC analysis, the purity of the obtained crystalline polymorph A of acetyl-glycine-beta-alanine was 99.4% (wavelength at 214 nm).

The crystalline polymorph A of acetyl-glycine-beta-alanine obtained in Example 1, Example 2, and Example 3 were analyzed by powder X-ray diffraction, Fourier transform infrared spectroscopy, and differential scanning calorimetry. All of them have the same analytical results described as follows:

Powder X-ray diffraction pattern having peaks at 10.4±0.2, 11.0±0.2, 12.9±0.2, 16.0±0.2, 16.4±0.2, 17.6±0.2, 19.1±0.2, 19.5±0.2, 20.0±0.2, 21.2±0.2, 23.2±0.2, 23.5±0.2, 24.1±0.2, 24.9±0.2, 25.3±0.2, 26.2±0.2, 27.9±0.2, 30.2±0.2, 39.5±0.2, and 40.1±0.2 2-theta degree, as shown in FIG. 1.

Fourier transform infrared spectrum having bands at 3315±2 cm$^{-1}$, 1697±2 cm$^{-1}$, 1670±2 cm$^{-1}$, 1543±2 cm$^{-1}$, 1441±2 cm$^{-1}$, 1376±2 cm$^{-1}$, 1277±2 cm$^{-1}$, 1248±2 cm$^{-1}$, 1144±2 cm$^{-1}$, 1089±2 cm$^{-1}$, 1071±2 cm$^{-1}$, 1044±2 cm$^{-1}$, 998±2 cm$^{-1}$, 983±2 cm$^{-1}$, 949±2 cm$^{-1}$, 888±2 cm$^{-1}$, 796±2 cm$^{-1}$, 712±2 cm$^{-1}$, 666±2 cm$^{-1}$, as shown in FIG. 3.

Differential scanning calorimetry (DSC) thermogram indicated two endotherm peaks at 168±2° C. and 177±2° C., as shown in FIG. 5.

B. Preparation of Crystalline Polymorph B of Acetyl-Glycine-β-Alanine

Example 4

20 grams of crude acetyl-glycine-beta-alanine, obtained from concentrating the mother liquid was mixed with 200 grams of isopropanol and 20 grams of water in a flask and stirred to form a mixture. The mixture was dissolved into a solution at about 70° C., and then cooled down for forming the crystalline polymorph B of acetyl-glycine-beta-alanine. The crystalline polymorph B of acetyl-glycine-beta-alanine was filtered at about 15° C. and was dried under vacuum. 18.1 grams of the crystalline polymorph B of acetyl-glycine-beta-alanine was obtained. According to HPLC analysis, the purity of the crystalline polymorph B of acetyl-glycine-beta-alanine was 99.1% (wavelength at 214 nm).

Figure 2:
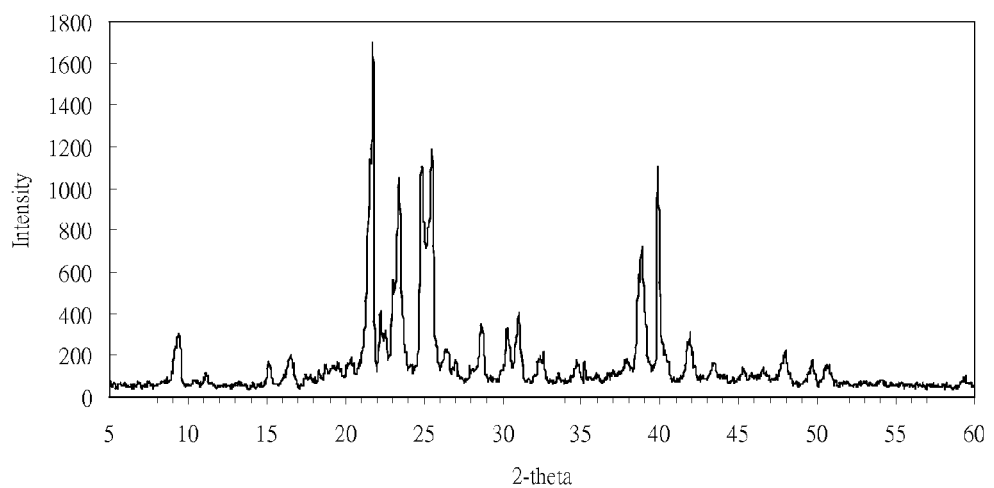
FIG. 2 is a characteristic powder X-ray diffraction pattern of crystalline polymorph B of acetyl-glycine-beta-alanine.

The crystalline polymorph B of acetyl-glycine-beta-alanine obtained in Example 4 exhibited a powder X-ray diffraction pattern having peaks at 9.3±0.2, 15.1±0.2, 16.5±0.2, 21.3±0.2, 22.4±0.2, 23.2±0.2, 24.6±0.2, 25.2±0.2, 26.1±0.2, 28.6±0.2, 30.4±0.2, 31.0±0.2, 32.1±0.2, 38.4±0.2, 40.0±0.2, and 41.6±0.2 2-theta degree, as shown in FIG. 2.

The Fourier transform infrared spectrum of the crystalline polymorph of acetyl-glycine-beta-alanine obtained in Example 4 having bands at 3309±2 cm$^{-1}$, 1699±2 cm$^{-1}$, 1662±2 cm$^{-1}$, 1601±2 cm$^{-1}$, 1548±2 cm$^{-1}$, 1436±2 cm$^{-1}$, 1375±2 cm$^{-1}$, 1313±2 cm$^{-1}$, 1265±2 cm$^{-1}$, 1206±2 cm$^{-1}$, 1132±2 cm$^{-1}$, 1080±2 cm$^{-1}$, 1046±2 cm$^{-1}$, 1014±2 cm$^{-1}$, 912±2 cm$^{-1}$, 786±2 cm$^{-1}$, 736±2 cm$^{-1}$, 688±2 cm$^{-1}$, as shown in FIG. 4.

The Differential scanning calorimetry (DSC) thermogram of the crystalline polymorph of acetyl-glycine-beta-alanine obtained in Example 4 indicating one endotherm peaks at 176±2° C., as shown in FIG. 6.

Long term storage stability can be found in both crystalline polymorph A and crystalline polymorph B of acetyl-glycine-beta-alanine. The powder X-ray diffraction pattern of the crystalline polymorph A and crystalline polymorph B are shown as FIG. 1 and FIG. 2, wherein the crystalline polymorph A and crystalline polymorph B were stored at room temperature for 1 year without any humidity controlling. The mentioned powder X-ray diffraction analytical result showed that both crystalline polymorph A and crystalline polymorph B of acetyl-glycine-beta-alanine were not changed by time without any humidity controlling.

Thermal Stability Study for Both of Crystalline Polymorph A and Crystalline Polymorph B of Acetyl-Glycine-Beta-Alanine:

The crystalline polymorph A of acetyl-glycine-beta-alanine and crystalline polymorph B of acetyl-glycine-beta-alanine were stored at 140° C. oven with air circulation for 4 hours, and then analyzed with powder X-ray diffraction. The powder X-ray diffraction pattern of crystalline polymorph A of acetyl-glycine-beta-alanine as shown as FIG. 7 was still not changed by the heated condition under the oxygen. And, it is found that the powder X-ray diffraction pattern of crystalline polymorph B of acetyl-glycine-beta-alanine as shown as FIG. 8 was changed.

Thermodynamic Stable Crystalline Polymorph Study: Slurry Equilibrium

According to the theory of thermodynamic of polymorphism, a slurry mixture of crystalline polymorphs will equilibrate to the most stable crystalline polymorph in a sufficient time.

Example 5

Both of 5 grams of crystalline polymorph A and 5 grams of crystalline polymorph B of acetyl-glycine-beta-alanine were put into a flask. 100 grams of isopropanol and 10 grams of water were added into the flask to form a mixture. The mixture was stirred at 40 to 45° C. for 8 hours and then at 25 to 30° C. for 48 hours. The mixture was cooled to 15 to 20° C. and the crystalline was filtered out. The crystalline was dried and analyzed with powder X-ray diffraction and Fourier transform infrared spectrum. The analytical results showed that the obtained crystalline was crystalline polymorph A of acetyl-glycine-beta-alanine.

The Solubility Study of Crystalline Polymorph A and Polymorph B of Acetyl-Glycine-Beta-Alanine According to the theory of thermodynamic of polymorphism, the most thermodynamic stable crystalline polymorph has lowest solubility. The solubility of both of the crystalline polymorph A and polymorph B of acetyl-glycine-beta-alanine were measured in different solvents.

The solubility measurement procedure was described as the following. Prepared a saturated acetyl-glycine-beta-alanine solution with 1 gram of test solvents and then stir it for 30 min at room temperature. Collected the solution through a filter and used HPLC to analyze its solubility. The result was shown as Table 1. The solubility was represented by mg of the polymorphs/grams of the solvent. The result showed that crystalline polymorph A of acetyl-glycine-beta-alanine was less soluble than crystalline polymorph B of acetyl-glycine-beta-alanine in various solvents. The results indicated crystalline polymorph A of acetyl-glycine-beta-alanine is thermodynamically stable

TABLE 1

| Test Solvent | Crystalline Polymorph A Solubility mg/g of solvent | Crystalline Polymorph B Solubility mg/g of solvent |
|---|---|---|
| Isopropanol/water: 3/1 (weight ratio) | 62.3 mg/g | 76.4 mg/g |
| Water | 177.0 mg/g | 223.2 mg/g |
| Methanol | 26.5 mg/g | 32.4 mg/g |
| Ethanol/water: 95/5 (weight ratio) | 18.4 mg/g | 23.9 mg/g |

In summary, this application has reported a novel crystalline polymorph of acetyl-glycine-beta-alanine and process of making the same. According to this invention, the mentioned crystalline polymorphs of acetyl-glycine-beta-alanine can exhibit novel behavior on their detected spectrum. Moreover, the process of forming the crystalline polymorphs of acetyl-glycine-beta-alanine can provide excellent purity of the crystalline polymorphs of acetyl-glycine-beta-alanine, so that the crystalline polymorphs can be applied in topical cosmetic compositions, pharmaceutical compositions as skin care preparations, or other functional preparations.

Obviously many modifications and variations are possible in light of the above teachings. It is therefore to be understood that within the scope of the appended claims the present invention can be practiced otherwise than as specifically described herein. Although specific embodiments have been illustrated and described herein, it is obvious to those skilled in the art that many modifications of the present invention may be made without departing from what is intended to be limited solely by the appended claims.

What is claimed is:

1. A crystalline polymorph of acetyl-glycine-beta-alanine wherein said crystalline polymorph is characterized with an X-ray powder diffraction pattern comprising peaks at 16.4±0.2, 21.2±0.2, 23.2±0.2, 24.9±0.2, 25.3±0.2, 26.2±0.2, 30.2±0.2, and 40.1±0.2 2-theta degree.

2. The crystalline polymorph of claim 1, wherein said X-ray powder diffraction pattern further comprises peaks at 10.4±0.2, 11.0±0.2, 12.9±0.2, 16.0±0.2, 17.6±0.2, 19.1±0.2, 19.5±0.2, 20.0±0.2, 23.5±0.2, 24.1±0.2, 27.9±0.2, and 39.5±0.2 2-theta degree.

3. The crystalline polymorph of claim 1, wherein said X-ray powder diffraction pattern further comprises peaks substantially as shown in FIG. 1.

4. The crystalline polymorph of claim 1, wherein said crystalline polymorph is characterized with a Fourier transform infrared spectrum comprising bands at 1697±2 $cm^{-1}$, 1376±2 $cm^{-1}$, and 1044±2 $cm^{-1}$.

5. The crystalline polymorph of claim 4, wherein said Fourier transform infrared spectrum further comprises bands at 3315±2 $cm^{-1}$, 1670±2 $cm^{-1}$, 1543±2 $cm^{-1}$, 1441±2 $cm^{-1}$, 1277±2 $cm^{-1}$, 1248±2 $cm^{-1}$, 1144±2 $cm^{-1}$, 1089±2 $cm^{-1}$, 1071±2 $cm^{-1}$, 998±2 $cm^{-1}$, 983±2 $cm^{-1}$, 949±2 $cm^{-1}$, 888±2 $cm^{-1}$, 796±2 $cm^{-1}$, 712±2 $cm^{-1}$, and 666±2 $cm^{-1}$.

6. The crystalline polymorph of claim 4, wherein said Fourier transform infrared spectrum further comprises bands substantially as shown in FIG. 3.

7. The crystalline polymorph of claim 1, wherein said crystalline polymorph is characterized with a differential scanning calorimetry (DSC) thermogram comprising a peak at 177±2° C.

8. The crystalline polymorph of claim 7, wherein said differential scanning calorimetry (DSC) thermogram further comprises a peak at 168±2° C.

9. A crystalline polymorph of acetyl-glycine-beta-alanine wherein said crystalline polymorph is characterized with a Fourier transform infrared spectrum comprising bands at 1697±2 $cm^{-1}$, 1376±2 $cm^{-1}$, and 1044±2 $cm^{-1}$.

10. The crystalline polymorph of claim 9, wherein said Fourier transform infrared spectrum further comprises bands at 3315±2 $cm^{-1}$, 1670±2 $cm^{-1}$, 1543±2 $cm^{-1}$, 1441±2 $cm^{-1}$, 1277±2 $cm^{-1}$, 1248±2 $cm^{-1}$, 1144±2 $cm^{-1}$, 1089±2 $cm^{-1}$, 1071±2 $cm^{-1}$, 998±2 $cm^{-1}$, 983±2 $cm^{-1}$, 949±2 $cm^{-1}$, 888±2 $cm^{-1}$, 796±2 $cm^{-1}$, 712±2 $cm^{-1}$, and 666±2 $cm^{-1}$.

11. The crystalline polymorph of claim 9, wherein said Fourier transform infrared spectrum further comprises bands substantially as shown in FIG. 3.

12. The crystalline polymorph of claim 9, wherein said crystalline polymorph is characterized with an X-ray powder diffraction pattern comprising peaks at 16.4±0.2, 21.2±0.2, 23.2±0.2, 24.9±0.2, 25.3±0.2, 26.2±0.2, 30.2±0.2, and 40.1±0.2 2-theta degree.

13. The crystalline polymorph of claim 12, wherein said X-ray powder diffraction pattern further comprises peaks at 10.4±0.2, 11.0±0.2, 12.9±0.2, 16.0±0.2, 17.6±0.2, 19.1±0.2, 19.5±0.2, 20.0±0.2, 23.5±0.2, 24.1±0.2, 27.9±0.2, and 39.5±0.2 2-theta degree.

14. The crystalline polymorph of claim 12, wherein said X-ray powder diffraction pattern further comprises peaks substantially as shown in FIG. 1.

15. The crystalline polymorph of claim 9, wherein said crystalline polymorph is characterized with a differential scanning calorimetry (DSC) thermogram comprising a peak at 177±2° C.

16. The crystalline polymorph of claim 15, wherein said differential scanning calorimetry (DSC) thermogram further comprises a peak at 168±2° C.

17. A crystalline polymorph of acetyl-glycine-beta-alanine wherein said crystalline polymorph is characterized with an X-ray powder diffraction pattern comprising peaks at 9.3±0.2, 15.1±0.2, 16.5±0.2, 21.3±0.2, 22.4±0.2, 23.2±0.2, 24.6±0.2, 25.2±0.2, 26.1±0.2, 28.6±0.2, 30.4±0.2, 31.0±0.2, 32.1±0.2, 38.4±0.2, 40.0±0.2, and 41.6±0.2 2-theta degree.

18. The crystalline polymorph of claim 17, wherein said crystalline polymorph is characterized with a Fourier transform infrared spectrum comprising bands at 3309±2 $cm^{-1}$, 1699±2 $cm^{-1}$, 1662±2 $cm^{-1}$, 1601±2 $cm^{-1}$, 1548±2 $cm^{-1}$, 1436±2 $cm^{-1}$, 1375±2 $cm^{-1}$, 1313±2 $cm^{-1}$, 1265±2 $cm^{-1}$, 1206±2 $cm^{-1}$, 1132±2 $cm^{-1}$, 1080±2 $cm^{-1}$, 1046±2 $cm^{-1}$, 1014±2 $cm^{-1}$, 912±2 $cm^{-1}$, 786±2 $cm^{-1}$, 736±2 $cm^{-1}$, 688±2 $cm^{-1}$.

19. The crystalline polymorph of claim 17, wherein said crystalline polymorph is characterized with a differential scanning calorimetry (DSC) thermogram comprising a peak at 176±2° C.

* * * * *